US011344661B2

(12) United States Patent
Laubrock et al.

(10) Patent No.: US 11,344,661 B2
(45) Date of Patent: May 31, 2022

(54) BLOOD TREATMENT WITH INACTIVATION OF CIRCULATING NUCLEIC ACIDS

(71) Applicant: FRESENIUS MEDICAL CARE DEUTSCHLAND GMBH, Bad Homburg (DE)

(72) Inventors: Andreas Laubrock, Wehrheim (DE); Rainer Fislage, St. Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 966 days.

(21) Appl. No.: 16/075,679

(22) PCT Filed: Feb. 9, 2017

(86) PCT No.: PCT/EP2017/052871
§ 371 (c)(1),
(2) Date: Aug. 6, 2018

(87) PCT Pub. No.: WO2017/137495
PCT Pub. Date: Aug. 17, 2017

(65) Prior Publication Data
US 2019/0046717 A1    Feb. 14, 2019

(30) Foreign Application Priority Data

Feb. 9, 2016  (DE) .................... 10 2016 001 407.5

(51) Int. Cl.
*A61M 1/36* (2006.01)
*A61M 1/34* (2006.01)
*C12N 11/12* (2006.01)

(52) U.S. Cl.
CPC ............ *A61M 1/3687* (2013.01); *A61M 1/34* (2013.01); *A61M 1/3482* (2014.02);
(Continued)

(58) Field of Classification Search
CPC .............. A61M 1/3687; A61M 1/3482; A61M 1/3486; A61M 1/3489; A61M 1/3689;
(Continued)

(56) References Cited

U.S. PATENT DOCUMENTS

| 4,824,432 A * | 4/1989 | Skurkovich ......... A61M 1/3679 424/130.1 |
| 2007/0092509 A1* | 4/2007 | Mittra ................. A61M 1/3693 424/140.1 |

(Continued)

FOREIGN PATENT DOCUMENTS

| EP | 1666055 A1 | 6/2006 |
| EP | 1655036 B1 | 7/2013 |

(Continued)

OTHER PUBLICATIONS

D.S. Terman et al., Degradation of Circulating DNA by Extracorporeal Circulation over Nuclease Immobilized on Nylon Microcapsules, The Journal of Clinical Investigation, 1976, 57:1201-1212 (Year: 1976).*

(Continued)

*Primary Examiner* — Philip R Wiest
(74) *Attorney, Agent, or Firm* — Kilyk & Bowersox, P.L.L.C.

(57) ABSTRACT

The present invention relates to a device for the treatment of blood comprising a solid phase on which a polypeptide is immobilized which is suitable for the inactivation of free nucleic acids. Suitable polypeptides are, for example, deoxyribonucleases, ribonucleases, DNA methyltransferases or cytosine deaminases. The invention further comprises the use of such devices for the treatment of patients suffering from chronic kidney failure, cancer or lupus erythematosus, as well as methods and systems for the treatment of blood, wherein free nucleic acids are inactivated outside the body.

16 Claims, 7 Drawing Sheets

Figure 1:
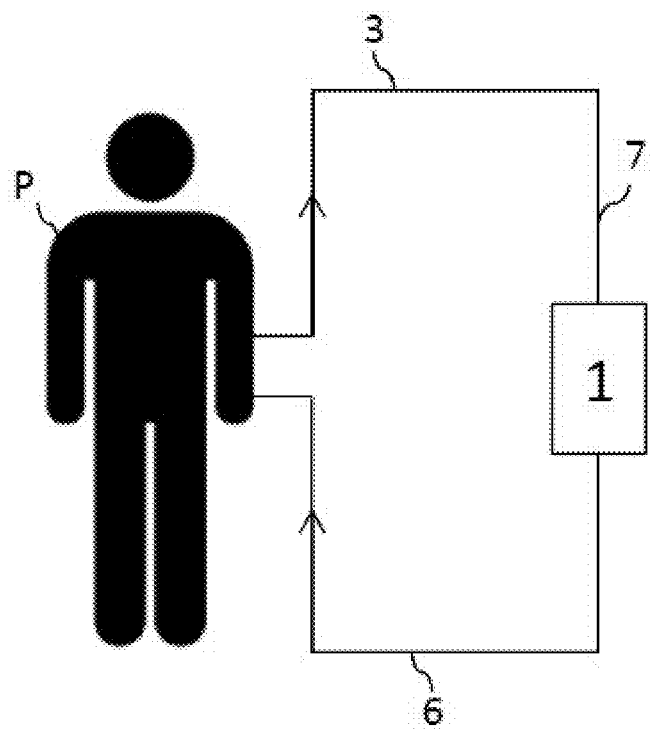

(52) U.S. Cl.
CPC ........ *A61M 1/3486* (2014.02); *A61M 1/3489* (2014.02); *A61M 1/36* (2013.01); *A61M 1/3689* (2014.02); *C12N 11/12* (2013.01); *A61M 2202/0415* (2013.01); *A61M 2202/20* (2013.01); *A61M 2202/203* (2013.01); *A61M 2202/206* (2013.01)

(58) Field of Classification Search
CPC .. A61M 1/34; A61M 1/36; A61M 2202/0415; A61M 2202/20; A61M 2202/203; A61M 2202/206
See application file for complete search history.

(56) References Cited

U.S. PATENT DOCUMENTS

2011/0125286 A1† 5/2011 Selden
2011/0125386 A1* 5/2011 Pursifull ............... F02D 41/221
 701/103
2012/0226258 A1 9/2012 Otto et al.

FOREIGN PATENT DOCUMENTS

RU 2441674 C1 † 2/2012
WO 2005025650 A1 3/2005

OTHER PUBLICATIONS

International Search Report issued in corresponding International Patent Application No. PCT/EP2017/052871 (with English translation) dated Apr. 24, 2017 (9 pages).
Lintern, Immobilisation of Lactate Oxidase, 209, 2013, University College London.†
Simakova, E.S., An Experimental Support of the use of Immobilized Deoxyribose of Type I in the Treatment of Systemic Lupus Erythematosus, 53, Sep. 15, 2011.†
Terman et al., The Journal of ClinicalInvestigation, 1976, 57:1201-1212.†
Trofimenko et al., Biomedical Chemistry, 2015, 61(5): 622-627.†

\* cited by examiner
† cited by third party

BLOOD TREATMENT WITH INACTIVATION OF CIRCULATING NUCLEIC ACIDS

This application is a National Stage Application of PCT/EP2017/052871, filed Feb. 9, 2017, which claims priority to German Patent Application No. 10 2016 001 407.5, filed Feb. 9, 2016.

The present invention relates to a device for the treatment of blood comprising a solid phase on which polypeptides are immobilized for the inactivation of free nucleic acids.

Patients who are treated with haemodialysis or peritoneal dialysis methods have increased levels of proinflammatory cytokines such as e.g. TNF-α, IL-6, IL-12 and IL-1β, which are released via the NFκB signalling pathway compared with the normal population. There are different explanations for the underlying cause. In any case, these increased concentrations of inflammatory substances are linked to poor survival of the patients in the case of chronic dialysis (Panichi V., Paoletti S. et al. Inflammatory pattern in hemodiafiltration. *Contrib. Nephroi.* 2008; 161: 185-190), with the result that the need exists to aetiologically suppress the induction of the underlying signal cascades. If the release of the proinflammatory cytokines can be suppressed, the patients' chances of survival are increased.

One of many known causes for the induction and release of proinflammatory cytokines is the contact between DNA circulating freely in the blood with receptors which recognize PAMP structures (pathogen associated molecular patterns). The associated PRR proteins (pattern recognition receptors) which detect the PAMP are a phylogenetically old, heterogeneous system of receptor molecules which recognizes basic structures of pathogens and emits corresponding signals to activate the immune system.

Thus, lipopolysaccharide (LPS, synonym: endotoxin) released, for example, from gram-negative bacteria induces the release of proinflammatory cytokines on contact with whole blood even in the smallest quantities. The recognition of the biologically active Lipid A moiety of the endotoxin is effected via the TLR-4 receptor (toll-like receptor), which is capable of recognizing the Lipid A structures of different species of bacteria although the latter differ in microstructure (Medzhitov R. M., Janeway C. Innate Immunity. *N. Engl. J. Med.* 2000; 338: 338-344).

Furthermore, phosphorylcholine groups present on bacteria cells are recognized by the C-reactive protein of human blood. By means of downstream, complement-mediated activation procedures proinflammatory cytokines are released in this case, too (Tillet, W. S., Francis T. J. Serological reactions in pneumonia with a non-protein somatic fraction of pneumococcus. *J. Exp. Med.* 1930; 52: 561-585. Black S., Kushner I. et al. C-reactive protein. *J. Biol. Chem.* 2004; 279: 48487-48490).

Another PRR, which bears the name TLR-9, was described for the recognition of DNA (Chi H., Flavell R. A. Innate recognition of non-self nucleid acids. *Genome Biol.* 2008; 9:211). It was previously shown that TLR-9 recognizes bacterial DNA and is activated by the latter. However, a reaction of TLR-9 to endogenous DNA of the human body was not yet known, for which reason the contamination of dialysate with bacterial DNA fragments was discussed in specialist circles (Kwan B. C. H., Chow K. M. et al. Effect of using ultrapure dialysate for hemodialysis on the level of circulating bacterial fragment in renal failure patients. *Nephron. Clin. Pract.* 2013; 123: 246-253. Schindler, R., Beck W. et al. Short bacterial DNA fragments: detection in the dialysate and induction of cytokines. *J. Am. Soc. Nephroi.* 2004; 15: 3207-3214).

However, it was also known that increased quantities of free apoptotic DNA are present in the blood of CKD patients. The precise origin of the DNA and its release mechanism have not yet been determined. Since freely circulating nucleic acids can also be detected in the blood of normal people, (Tamkovich, S. N., Bryzgunova, O. E. et al. Circulating nucleic acids in blood of healthy male and female donors. *Clin. Chem.* 2005; 7: 1317-1319), the possibility exists either that increased formation rates are present in CKD patients because of increased apoptosis, or that the degradation of the DNA is inhibited here. In particular as a result of the uraemic metabolic status of the patients substances might form which inhibit the activity of deoxyribonucleases, i.e. precisely the enzymes which are responsible for the degradation of DNA. Recently it was possible to show that this free DNA is responsible for the release of proinflammatory cytokines (Atamaniuk J., Kopechky C. et al. Apoptotic cell-free DNA promotes inflammation in haemodialysis patients. *Nephrol. Dial. Transplant.* 2011; 0: 1-4).

References to the origin of the free DNA are also found in the field of cardio-vascular research. Here it was proven that it is not the genomic human DNA from apoptotic degradation processes which is responsible for the cytokine induction but intracellular localized mitochondrial DNA (mtDNA) (Oka T., Hikoso S. et al. Mitochondrial DNA that escapes from autophagy causes inflammation and heart failure. *Nature.* 2012; 485: 251-255). This means, analogously, that in the blood of CKD patients not only bacterial DNA fragments are responsible for the cytokine induction but above all human mitochondrial DNA which is present in the blood at least partially in free form.

For phylogenetic reasons (symbiotic theory) mitochondrial DNA, like bacterial DNA, has a statistically underrepresented CpG dinucleotide which, moreover—in contrast to genomic DNA—is only methylated to a minor degree. Because of this similarity to a PAMP (non-methylated CpG dinucleotides), freely circulating mitochondrial DNA can thus activate the TLR-9 receptor which in turn then induces the cytokine synthesis.

Freely circulating DNA also plays a role in the clinical picture of lupus erythematosus (LE), a genetic autoimmune disease. Thus, free nucleic acids which induce the formation of anti-DNA antibodies and thus cause the release of cytokine and inflammatory reactions were detected in the blood of LE patients (Tan E. M., Schur P. H. et al. Deoxyribonucleic acid (DNA) and antibodies to DNA in the serum of patients with systemic lupus erythematosus. *J. Clin. Invest.* 1966; 46: 1732-1740). These anti-DNA antibodies also make a substantial contribution to renal symptoms in LE patients (Termaat, R. M., Asmann, M. et al. Anti-DNA antibodies can bind to the glomerulus via two distinct mechanisms. *Anti-DNA antibodies.* 1992; 61).

Increased concentrations of another type of free nucleic acids, namely mRNAs, were described in cancer patients (Tani N., Ichikawa D. et al. Circulating Cell-free mRNA in Plasma as a Tumor Marker for Patients with Primary and Recurrent Gastric Cancer. *Anticancer Research.* 2007; 27: 1207-1212. Garcia V., Garcia, J. M. et al. Free circulating mRNA in plasma from breast cancer patients and clinical outcome. *Cancer Letters.* 2008; 263: 312-320. March-Villaalba J. A., Martinez-Jabaloyas J. M. et al. Cell-Free Circulating Plasma hTERT mRNA Is a Useful Marker for Prostate Cancer Diagnosis and Is Associated with Poor Prognosis Tumor Characteristics. *PLoS One.* 2012; 7(8): e43470). It is known that inflammatory reactions generally contribute to tumour progression (Coussens L. M., Werb Z., Inflammation and cancer. *Nature.* 2002; 420: 860-867). More recent studies furthermore suggest that, also in the case of cancer, inflammatory conditions are caused by the activation of PRRs such as the TLR-7 receptor (Chatterjee S., Crozet L. et al. TLR7 Promotes Tumor Progression, Chemotherapy Resistance, and Poor Clinical Outcomes in Non-Small Cell Lung Cancer. *Cancer Res.* 2014; 74: 5008-5018). Free nucleic acids such as mRNAs are also considered here as mediator of the inflammatory reactions.

It therefore ensues that the induction of the proinflammatory cytokine system can be prevented by inhibiting the biological effect of freely circulating nucleic acids in the named clinical pictures. This inhibition can be achieved by targeted inactivation of the nucleic acids, for example by direct degradation on solid phase or degradation in the liquid phase or by methylation or deamination of the DNA, whereby the PAMP motif is rendered unrecognizable and the TLR-9 can no longer be activated and thus the cytokine synthesis can no longer be induced.

In the state of the art it is described that DNaseI, a deoxyribonuclease, can be administered to cancer patients in order to degrade DNA circulating freely in the blood (EP 1655036 B1). However, this method harbours numerous risks and problems as the corresponding enzyme enters directly into the patient's body. On the one hand, a relatively high dose is necessary in order to achieve a corresponding effect at all. On the other hand, side effects which are caused for example by the active enzyme entering cells, cannot be ruled out.

The object of the present invention is therefore to provide devices and methods in order to inactivate nucleic acids circulating freely in the blood in an improved manner.

The invention achieves this object by providing a device for the treatment of blood containing
(a) tubes for whole blood or plasma to flow through from and to the patient and
(b) a solid phase on which a polypeptide is immobilized which is suitable for the inactivation of free nucleic acids.

The solid phase of the device according to the invention, on which the polypeptide is immobilized, can be either a hollow fibre membrane or beads or a non woven. Within the framework of the present invention, the membrane can consist of para-methoxymethamphetamine (PMMA), cellulose, ester, polyamide, polymethylsulfonate, polyetherimide, polyethersulfone or polysulfone alone or mixed with polyethylenimine, polyvinylpyrrolidone (PVP) or copolymers. Furthermore, the membrane can carry additional modifications or be unmodified. The number of layers of the membrane is not limited; an embodiment with a hollow fibre membrane with three layers is particularly preferred.

The polypeptide can be immobilized in different ways which are known from the state of the art. In order to obtain optimal enzymatic activity in the case of solid-phase-immobilized enzymes, a linker of an optimum length is normally required. The optimal length of this spacer is dependent on the type of the surface and on the type of the enzyme and can easily be determined by a person skilled in the art.

A solid phase according to the invention can preferably be obtained by spinning a polymer-bound polypeptide.

Furthermore, the solid phase according to the invention can be obtained by immobilizing the polypeptide on the surface of hollow fibre membranes. For this, methods are considered which are based on the presence of activated, activatable or reactive chemical functions on the inner surface of the membrane. As activatable groups OH and COOH groups are considered among others. $NH_2$ or $SH_2$ groups on a surface can also be reacted with a chemically activated group of a ligand.

There is an example in U.S. Pat. No. 4,177,038. In addition to the method described there, which can be used for example in the case of cellulose-based membranes, there is also the possibility of using carboxyl-modified polysulfones or polyethersulfones alone or non-modified polysulfones in combination with carboxyl-modified PVP derivatives.

For example, a solid phase according to the invention can be obtained by:
  spinning a carboxyl-containing polymer based on polysulfone or PVP
  preparing solid phases from the fibre bundles produced in this way
  conditioning the solid phases with a steam jet, rinsing and drying
  activating the carboxyl groups with a solution of EDC and optionally N-hydroxysuccinimide
  inserting a linker with a length e.g. of 6 carbon atoms (aminocaproic acid)
  activating the terminal carboxyl group again with EDC and subsequently reacting with a polypeptide solution to immobilize the polypeptide-amino groups (lysines) of the polypeptide are used for the covalent binding to the activated carboxyl group of the polymer
  rinsing the solid phase and gentle drying
  sterilizing the solid phase with gamma radiation or preferably the E-beam process.

Within the framework of the present invention, the term "inactivation of free nucleic acids" comprises all enzymatic activities which are suitable for inhibiting the biological activity of free nucleic acids. In one aspect of the invention, this includes the decomposition or degradation of the free nucleic acids by cleaving the phosphodiester bond between the nucleotides of the free nucleic acids. In another aspect, inactivation comprises rendering immunogenic motifs of the free nucleic acids unrecognizable, for example by methylating unmethylated CpG dinucleotides or by converting a cytosine into uracil by deamination.

Because the inactivation of the free nucleic acids is effected outside the body, side effects due to the activity of the polypeptide in the body are ruled out. Moreover, the device can be used multiple times which makes the therapy particularly cost-effective in comparison with the direct administration of the corresponding polypeptide.

Within the framework of the invention, the term "free nucleic acids" comprises all of the types of cell-free nucleic acids which circulate in the blood. The origin of the free nucleic acids is not limited. It is conceivable that the free nucleic acids originate either from apoptotic or necrotic cells or are secreted by intact cells. Free nucleic acids can consist both of human genomic or mitochondrial DNA or of mRNA. Also comprised are viral as well as bacterial DNA, single- and double-stranded RNA as well as fragments thereof, which enter the patient's bloodstream for example during an infection. The free nucleic acids which are inactivated by means of the present invention can both be bound to proteins or be stabilized by them. The length of the free nucleic acids is not limited and ranges from 20 nucleotides/base pairs to several million base pairs. In one embodiment, the free nucleic acids to be inactivated have an inflammatory effect.

According to the invention, the biological activity of the free nucleic acids is suppressed by enzymatic inactivation on the solid phase. Suitable polypeptides are used for this. In an embodiment, deoxyribonucleases and/or ribonucleases are immobilized on the solid phase. These enzyme classes comprise both endonucleases and exonucleases. In a preferred embodiment, the human-identical endonuclease DNaseI is used, which is used under the trade name "Pulmozyme" for example to degrade macromolecular DNA in the lungs of patients with cystic fibrosis. According to the invention, different types of polypeptides with nuclease activity can also be immobilized at the same time. In a preferred embodiment DNaseI can for example be used together with an exonuclease which leads to a substantially increased reduction in the molecular weight of the DNA and to a better dialyzability of the fragments of the free nucleic acids.

In a further embodiment, the immobilized polypeptide is an enzyme the activity of which results in the motif of unmethylated CpG dinucleotides being rendered unrecognizable, such as e.g. cytosine deaminases and DNA methyltransferases. A preferred example of a DNA methyltransferase is human DNMT1.

Within the framework of the present invention, the use of enzymes and polypeptides which correspond in their protein sequence to the human one are preferred because the formation of antibodies can thus be prevented in the case of multiple use. Furthermore, the use of polypeptides which have e.g. a greater heat or solvent stability or other improved properties is also considered. A person skilled in the art knows how such mutants can be generated via targeted mutagenesis and how they can be examined in terms of their properties.

According to the invention, the term "polypeptides" comprises, in addition to the enzymes with the whole sequence, also shortened and changed variants of the named enzymes which exhibit the desired functionality. The variants here have a sequence homology of 60, 65, 70, 75, 80, 85, 90, 92, 95 or 100%. The variants preferably have a sequence homology of 75, 80, 85, 90, 92, 95 or 100%. Individual domains of the corresponding enzymes can also be used if these have the necessary catalytic activity. Methods of measuring the catalytic (residual) activity of a polypeptide are known sufficiently to a person skilled in the art and comprise functional assays, activity assays and assays with chemiluminescent or fluorescent substrates or substrates the reaction of which causes spectrophotometric changes.

In a further embodiment, short peptide sequences with the desired enzymatic activity are used. Peptides with nuclease activity are described, for example, in WO 02/40631 A2. Such peptides have the advantage of withstanding a technical sterilization process. A person skilled in the art can also measure the corresponding enzymatic activity of these peptides with known means.

The tubes of the device according to the invention can be connected directly to a patient. Alternatively, further tubes can be provided via which the patient is in fluid connection with the device. The tubes are used for whole blood or plasma to flow through.

In an embodiment, the device according to the invention further contains a dialyzer or haemofilter. Dialysis and haemofiltration methods are known to a person skilled in the art and refer in this connection to all methods which eliminate undesired substances from the body fluids of patients affected by a lack of or reduced renal excretory function using separating membranes.

This includes the haemodialysis method in which the undesired substances are removed from the blood by bringing the blood into contact with a dialysate. Polymer membranes which allow a diffusive and convective exchange of material are used as separating limit between blood and dialysate.

The peritoneal dialysis method can also be used. Here, the patient's peritoneum serves as separating limit for the exchange of material. In this case, the abdominal membrane separates the dialysate introduced into the abdomen from the body fluids of the patient. The exchange of material takes place substantially diffusively.

There are a plurality of technical variations of the named dialysis methods which follow the basic principle described. For physiological reasons it is common to all methods that no substances with a molecular weight of above approximately 69 kDa, the molecular weight of albumin, are removed permanently from the body of the patient. Because of the high molecular weight of double-stranded DNA of approximately 650 Da/base pair (bp), even short DNA fragments in the range of from 100 bp can no longer be effectively separated by a dialysis membrane with a separating limit of 69 kDa.

In addition to static systems, systems which can be worn on the patient, which are known by the abbreviation "WAK" (wearable artificial kidney), are also known according to the state of the art, or portable systems, which although they are operated in one place, can be easily transported.

Within the framework of the present invention, the solid phase with the immobilized polypeptide can be upstream of the dialyzer or haemofilter or can be located within the dialyzer or haemofilter. In the first case, the solid phase with the immobilized polypeptide and the dialyzer or haemofilter are in fluid connection via tubes. In each case, the fragments of the inactivated free nucleic acids can be removed from the whole blood or blood plasma during the dialysis.

In a further embodiment, the device for the treatment of blood furthermore contains a plasma filter. This can, for example, be a plasma filter which filters the whole blood coming from the patient in the front part via a pressure gradient, while the cleansed plasma is back-filtered in the rear part and thus fed back to the patient after passing through the dialyzer. The device for filtering plasma from the whole blood can also be a cell separator, for example a centrifuge. The device for filtering plasma serves to retain the cellular components of the blood which may possibly interfere with the inactivation of the free nucleic acids. In addition, it is thus possible to prevent the immobilized polypeptide from damaging the blood cells.

The object is furthermore achieved by the use of the device according to the invention for the treatment of proinflammatory conditions in patients suffering from chronic kidney failure, cancer or lupus erythematosus. By removing the free nucleic acids which are recognized by the innate immune system, the release of proinflammatory cytokines can be inhibited in all three clinical pictures and thus the inflammatory reaction in the patient can be reduced.

Furthermore, the invention comprises a method for the treatment of blood, wherein free nucleic acids are inactivated outside the body. In one embodiment, the method according to the invention can comprise the following steps:
  (i) providing a device according to the invention; and
  (ii) conveying the whole blood or blood plasma of a patient through the device under conditions which make it possible to inactivate the free nucleic acids by means of the polypeptide immobilized on the solid phase.

In particular, an appropriate flow rate, an operating temperature which allows an optimal enzyme activity and a sufficiently high density of immobilized polypeptide are to be ensured here. According to the invention, step (ii) of the method can be repeated in order to achieve a better inactivation of the free nucleic acids.

In a further embodiment, the method according to the invention can additionally comprise a step (ia) of filtering the blood plasma from the whole blood.

Because dialysis and inactivation of the free nucleic acids are combined in the preferred embodiment of the method according to the invention, the fragments of the free nucleic acids which are formed by the activity of the polypeptide can be filtered out of the blood plasma or whole blood during the treatment of the blood.

The invention further comprises a system for the treatment of blood comprising an extracorporeal circulation which contains a device according to the invention. The system can contain additional elements such as body fluid conveyors, pumps, filters, adsorbers, control elements, measuring and input units and data lines. It is considered that the system consists of several fluid circuits.

In a preferred embodiment, the system according to the invention is used for the treatment of proinflammatory conditions in patients suffering from chronic kidney failure, cancer or lupus erythematosus.

The invention is further explained in more detail with reference to figures and examples, without these being understood as limiting. There are shown in:

FIG. 1: a schematic block diagram of an embodiment of a device according to the invention in which the polypeptide is immobilized on a solid phase on bead material or non-woven without the additional connection of a dialyzer and without plasma separation.

Figure 2:
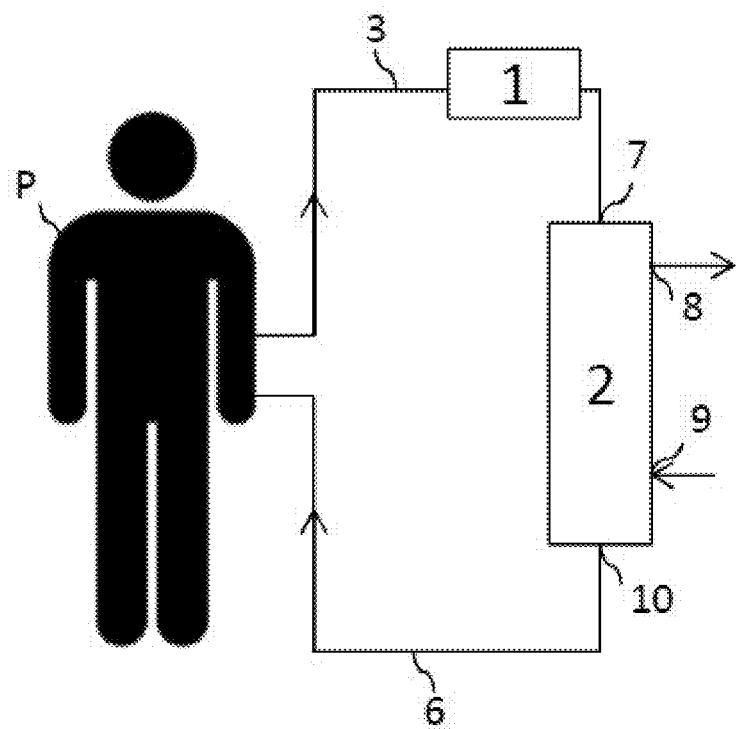

FIG. 2: a schematic block diagram of an embodiment of a device according to the invention in which the polypeptide is immobilized on a solid phase on bead material or non-woven outside the dialyzer.

Figure 3:
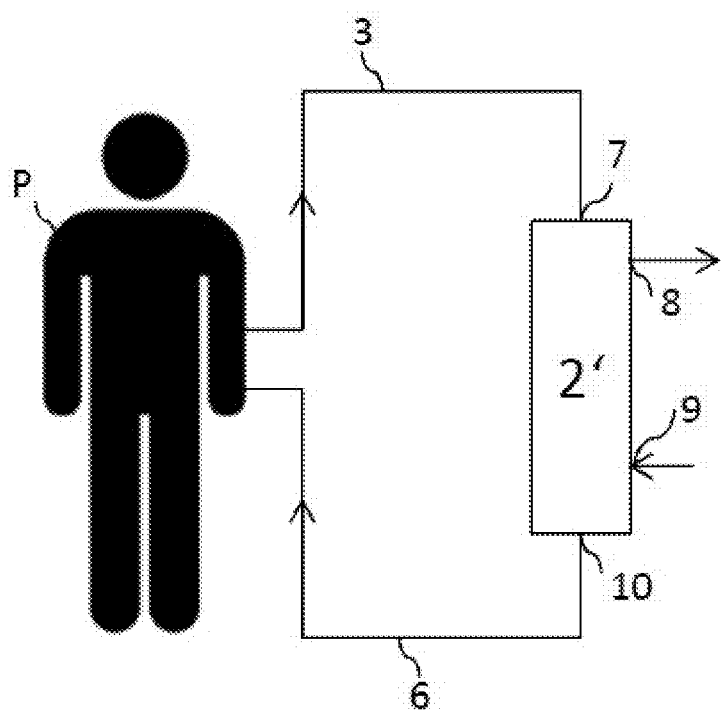

FIG. 3: a schematic block diagram of an embodiment of a device according to the invention with a multilayer hollow fibre membrane in which the polypeptide is immobilized on the side of the lumen.

Figure 4:
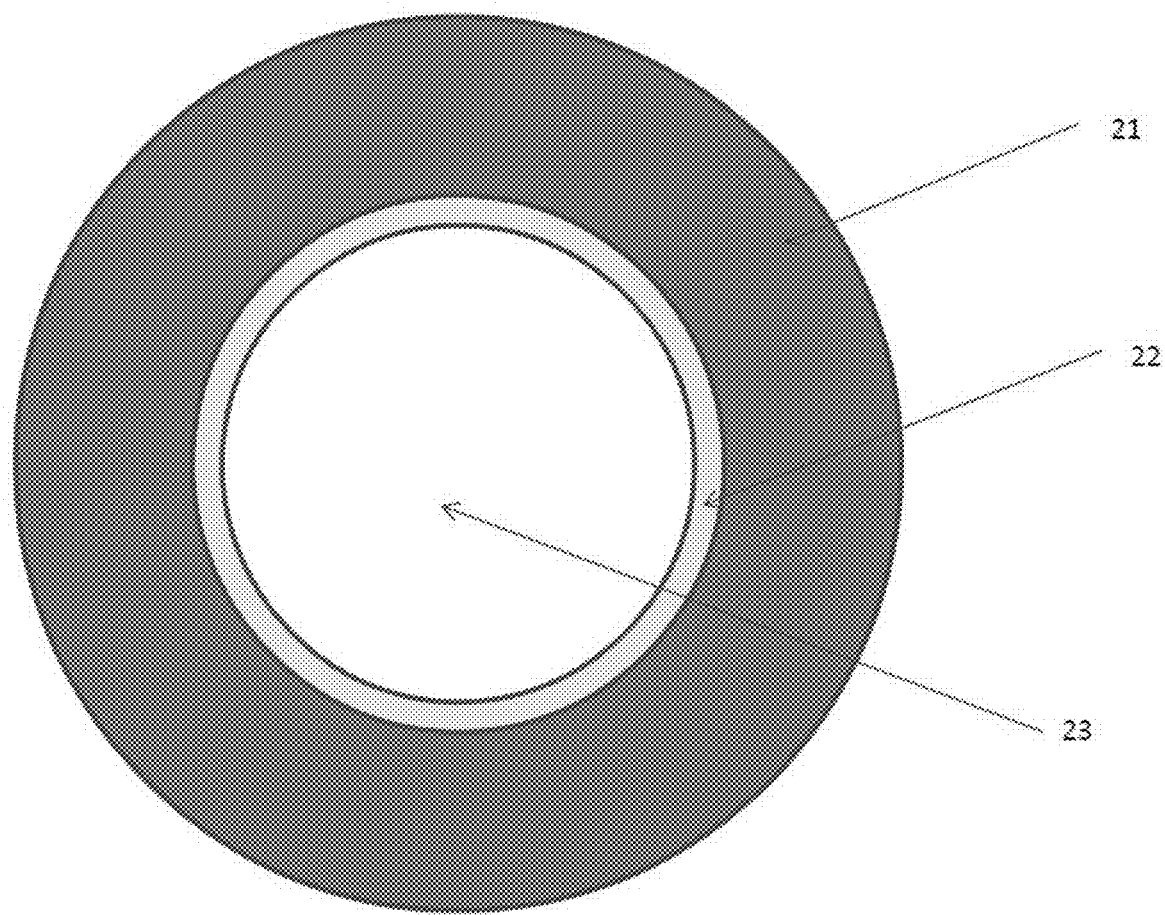

FIG. 4: diagram of a multilayer hollow fibre membrane according to the invention in which the polypeptide is immobilized on the side of the lumen.

Figure 5:
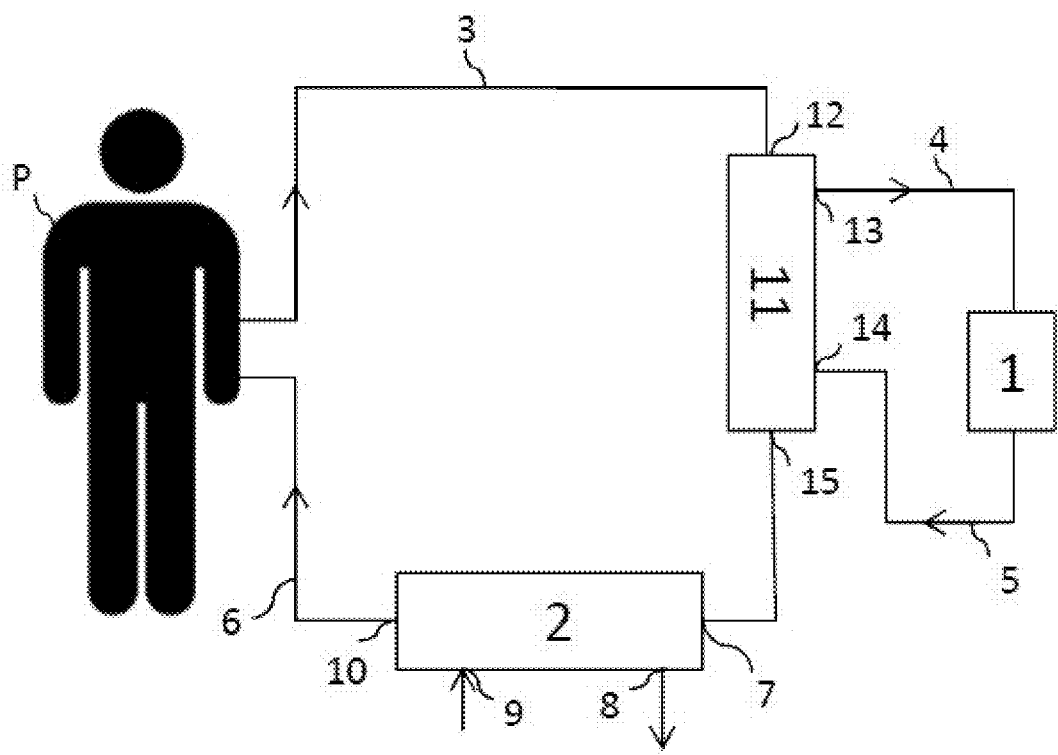

FIG. 5: a schematic block diagram of an embodiment of a device according to the invention in which a plasma separation additionally takes place.

Figure 6:
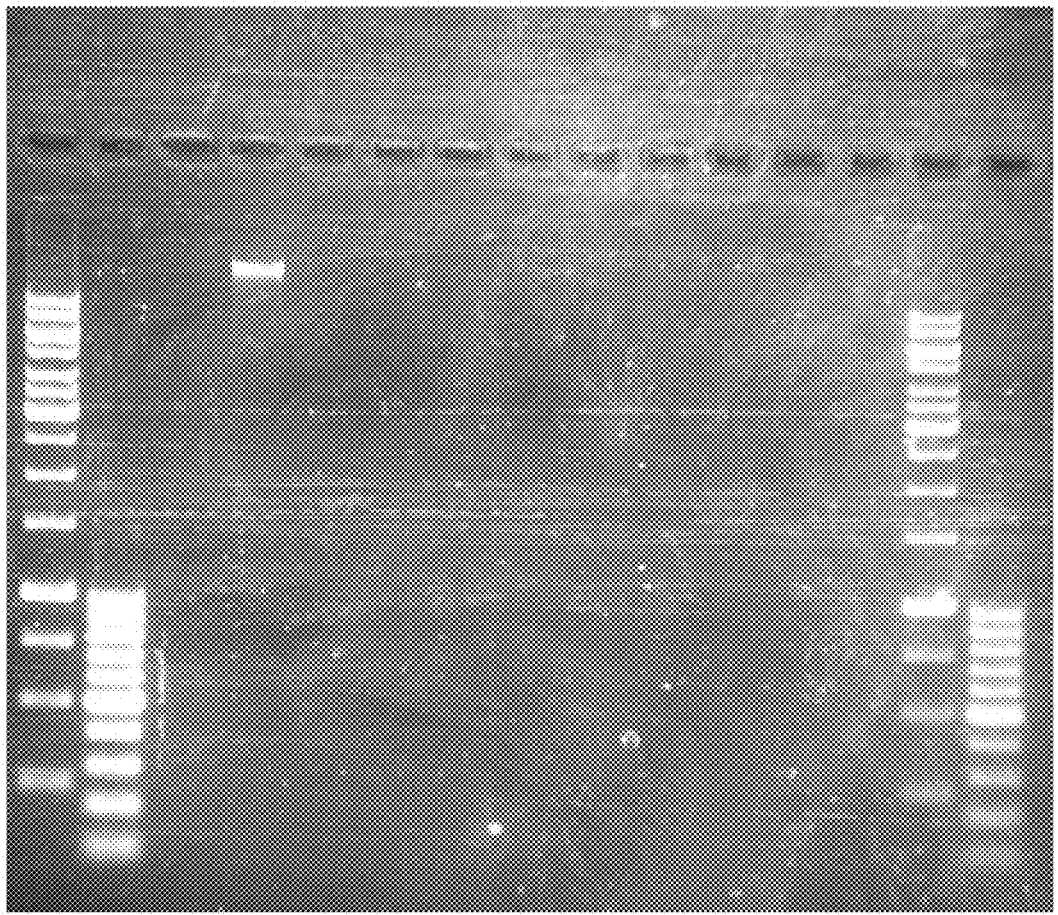

FIG. 6: agarose gel image of the treatment of chromosomal human DNA with DNaseI.

Figure 7:
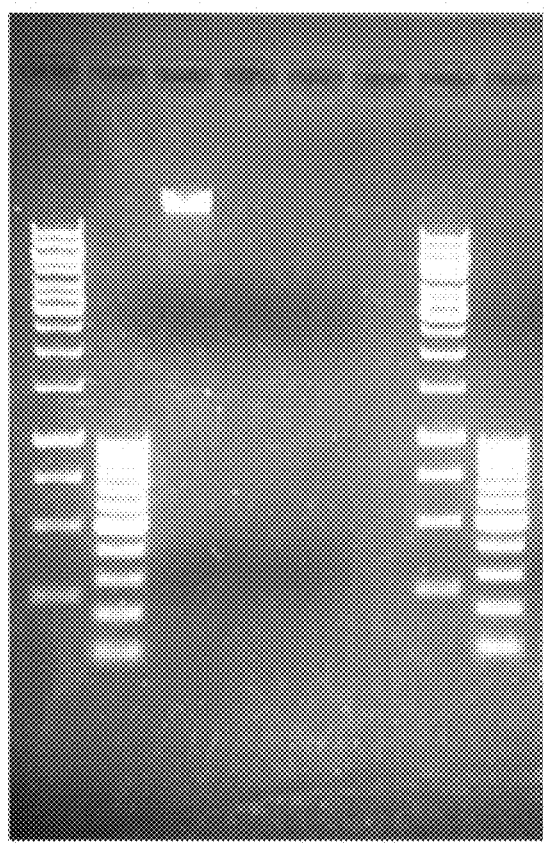

FIG. 7: agarose gel image which shows the effectiveness of immobilized DNaseI on fibre material.

In FIG. 1, a further embodiment of the device according to the invention is represented schematically. The reference numbers of this figure are assigned as reproduced below:
1 solid phase on which a polypeptide is immobilized
3 tube leading from the patient
6 tube leading to the patient The whole blood or blood plasma is conveyed via the tube 3 to the solid phase 1 on which a polypeptide for the inactivation of the free nucleic acids is immobilized according to the invention. After the free nucleic acids have been inactivated, the whole blood or blood plasma is conveyed back into the patient P.

In FIG. 2, an embodiment of a device according to the invention is represented schematically in which the inactivation of the free nucleic acids and dialysis take place separately. The reference numbers of this figure are assigned as reproduced below:
1 solid phase in the form of coated bead material or with coated non-woven
2 dialyzer
3 tube leading from the patient
6 tube leading to the patient
7 blood inlet
8 dialysate outlet
9 dialysate inlet
10 blood outlet
P patient In this embodiment, the blood is first conveyed over a solid phase 1 in the form of coated bead material or coated non-woven fabric on which the polypeptide is immobilized. Here, the free nucleic acids contained in the blood are degraded. After passage through the solid phase 1, the blood is conveyed further through the dialyzer 2 where the fragments of the free nucleic acids are dialyzed out.

In FIG. 3, an embodiment of a device according to the invention is represented schematically in which the polypeptide is immobilized on the side of the lumen on a multilayer hollow fibre membrane within the dialyzer. The reference numbers of this figure are reproduced as follows:
2' dialyzer with polypeptide immobilized on the side of the lumen
3 tube leading from the patient
6 tube leading to the patient
7 blood inlet
8 dialysate outlet
9 dialysate inlet
10 blood outlet
P patient The tube 3 has a first and second end, wherein the first end can be connected to the patient P and the second end is connected to the blood inlet 7 of the dialyzer 2'. The dialyzer 2' has as solid phase a multilayer hollow fibre membrane on which the polypeptide is immobilized on the side of the lumen. The tube 6 has a first and a second end, wherein the first end is connected to the blood outlet 10 of the dialyzer 2' and the second end can be connected to the patient P. The whole blood which enters through the blood inlet 7 is dialyzed in the dialyzer 2', wherein at the same time the immobilized polypeptide inactivates the free nucleic acids; the fragments are dialyzed out of the blood during the dialysis procedure. The whole blood can exit again via the blood outlet 10 and is fed back to the patient via the tube 6. The dialysate is introduced into and carried from the dialyzer 2' via the dialysate inlet 9 and the dialysate outlet 8, respectively.

In FIG. 4, the structure of a solid phase according to the invention in the form of a multilayer hollow fibre membrane in which a polypeptide is immobilized on the side of the lumen is shown schematically. The reference numbers of this figure are assigned as reproduced below:
21 outer layer of the membrane material
22 inner layer of the membrane material
23 lumen of the hollow fibre membrane The polypeptide is immobilized on the inner layer 22.

In FIG. 5, a further embodiment of the device according to the invention comprising a plasma separator is represented schematically. The reference numbers of this figure are assigned as reproduced below:
1 solid phase on which a polypeptide is immobilized
2 dialyzer
3 tube leading from the patient
4 connecting tube
5 connecting tube
6 tube leading to the patient 7 blood inlet
8 dialysate outlet
9 dialysate inlet
10 blood outlet
11 plasma filter
12 fluid feed inlet of the unfiltered side
13 fluid removal outlet of the unfiltered side
14 fluid feed inlet of the filtered side
15 fluid removal outlet of the filtered side
P patient The tube 3 has a first and second end, wherein the first end can be connected to the patient P and the second end is connected to the fluid feed inlet 12 of an unfiltered side of a filter 11. In addition to the unfiltered side, the plasma filter 11 has a filtered side, wherein the unfiltered side is separated from the filtered side by at least one filter material. The tube 6 has a first and a second end, wherein the first end is connected to the fluid removal outlet 10 of the dialyzer 2 and the second end can be connected to the patient P. The whole blood which enters through the fluid inlet of the unfiltered side 12 can exit again in part as blood plasma through the fluid removal outlet 13 of the filtered side. Via the tube 4, the separated blood plasma is then conveyed through the solid phase 1 on which a polypeptide is immobilized according to the invention. The immobilized polypeptide ensures that the free nucleic acids contained in the blood plasma are inactivated. The blood plasma with the inactivated free nucleic acids then flows via the tube 5 and enters the plasma filter 11 again at the fluid feed inlet of the filtered side 14 and exits through the fluid removal outlet 15 of the unfiltered side. The whole blood is then conveyed through a dialyzer 2 in which at the same time the fragments of the degraded free nucleic acids can be dialyzed out. After passage through the dialyzer 2, the cleansed whole blood is conveyed back into the patient P again.

In FIG. 6, an agarose gel image can be seen which shows the treatment of human chromosomal DNA with DNaseI. The samples were applied as follows (from left to right): 10 µl 1 kB ladder, 10 µl 100 bp ladder, empty, untreated DNA, 2 U DNaseI, empty, 0.5 U DNaseI, empty, 0.05 U DNaseI, empty, 0.005 U DNaseI, empty, 5 µl 1 kB ladder, 5 µl 100 bp ladder.

In FIG. 7, an agarose gel image can be seen which shows the effectiveness of immobilized DNaseI. The samples were applied as follows (from left to right): 10 µl 1 kB ladder, 10 µl 100 bp ladder, 400 ng untreated DNA, empty, 400 ng DNA after dialyzer passage, empty, 5 µl 1 kB ladder, 5 µl 100 bp ladder.

EXAMPLE 1

Treatment of Chromosomal Human DNA with DNaseI

Macromolecular human DNA was obtained from whole blood after lysis of the erythrocytes using the phenol-chloroform method.

In each case, 800 ng of this DNA were incubated at 37° C. for 10 min with different activities of a commercial DNaseI preparation. The reactions were stopped at the end of the reaction time by adding loading buffer with 5 mM EDTA and then 175 ng per lane was applied to a 1% agarose gel (Tris/Acetate/EDTA buffer, 110 V, 2 h). A 1 kB ladder served as molecular weight standard with 10 kB as highest molecular weight; a 100 bp ladder and 175 ng undigested genomic DNA served as reference.

After running the gel, ethidium bromide solution was used for staining and the gel was documented by photograph under UV illumination.

Result: Even at a concentration of only 0.005 U DNaseI, 800 ng DNA are completely degraded in 10 min at 37° C., as can be clearly identified by the lack of the typical degradation pattern. In the case of a partial degradation of the DNA, a clearly identifiable staining would have been identified in the affected lanes in the range of 10 kbp and below. In the untreated reference, these degradation products can be identified slightly above the 10 kbp band (cf. FIG. 6).

EXAMPLE 2

Preparation of Enzyme-Coated Hollow Fibres

Hollow fibres for the use of the nucleases according to the invention can be prepared according to the methods from DE 10 2011 010 921 A1 and DE 10 2008 003 090 A1. The membranes described there contain cellulose esters on their lumen-side layer which can be converted into cellulose either completely or partially by a treatment with dilute sodium hydroxide solution lasting approximately 30 min. The cellulose can be prepared for binding biological molecules by chemical activation. The techniques used are described in U.S. Pat. No. 4,177,038.

The DNaseI to be immobilized is used in 5-fold excess for the coupling reaction.

EXAMPLE 3

Effectiveness of Immobilized DNaseI on Fibre Material

In order to test the efficiency of DNaseI which is immobilized on a hollow fibre membrane, 3600 U/m² DNaseI was immobilized on a hollow fibre dialyzer with a lumen surface area of 1.4 m². 500 ml fresh test blood to which 500 µg human DNA was added was pumped through this hollow fibre dialyzer at 37° C. in a single pass at a lumen flow of 150 ml/min. The internal diameter of the fibres of the hollow fibre dialyzer was 185 µm and the residence time of the fluid in the dialyzer was 28 s. The dialysate side of the dialyzer was filled with isotonic dialysate which had physiological concentrations of mono- and divalent cations, in particular calcium and magnesium.

For the analysis on an agarose gel, a sample was taken after passage through the dialyzer. The volume of the sample was chosen such that an absolute quantity of 400 ng of genomic DNA was applied to the gel. The same quantity of untreated genomic DNA served as reference.

Result: After passage through the dialyzer, the genomic DNA was completely degraded which is clearly identifiable in the lack of typical degradation products below 10 kbp (cf. FIG. 7).

The invention claimed is:
1. A device for the treatment of blood, comprising:
(a) tubes for whole blood or blood plasma to flow through from and to the patient;
(b) a solid phase on which a polypeptide is immobilized which is suitable for the inactivation of free nucleic acids; and
(c) a dialyzer or haemofilter, wherein
the solid phase is upstream the dialyzer or haemofilter, or the solid phase is located within the dialyzer or haemofilter.

2. The device according to claim 1, wherein the polypeptide is selected from the group consisting of deoxyribonucleases, ribonucleases, endonucleases, exonucleases, endoribonucleases, exoribonucleases or peptides with nuclease activity.

3. The device according to claim 1, wherein the polypeptide is selected from the group consisting of DNA methyltransferases 1 (DNMT1) or peptides with methyltransferase activity.

4. The device according to claim 1, wherein the polypeptide has a cytosine deaminase activity.

5. The device according to claim 1, wherein the device furthermore comprises (d) a plasma filter.

6. The device according to claim 1, wherein the solid phase on which the polypeptide is immobilized comprises a hollow fibre membrane, beads or a non-woven.

7. The device according to claim 1, wherein the free nucleic acids to be inactivated have an inflammatory effect.

8. The device according to claim 1, wherein the free nucleic acids to be inactivated are selected from the group consisting of human genomic DNA, mitochondrial DNA (mtDNA) or mRNA.

9. The device according to claim 1, wherein the free nucleic acids to be inactivated are selected from the group consisting of bacterial or viral DNA or RNA.

10. A method for treating proinflammatory conditions in patients suffering from chronic kidney failure, cancer or lupus erythematosus, said method comprising inactivating free nucleic acids of said patients by treating blood of said patients with the device of claim 1.

11. A method for the treatment of blood, wherein free nucleic acids are inactivated outside the body, said method comprising treating the blood with the device of claim 1.

12. The method according to claim 11, further comprising the step of conveying the whole blood or blood plasma of the patient through the device under conditions which make it possible to inactivate the free nucleic acids by means of the polypeptide immobilized on the solid phase.

13. The method according to claim 11, further comprising a step of filtering the blood plasma from the whole blood.

14. The method according to claim 11, wherein the inactivated free nucleic acids are removed from the whole blood or blood plasma by means of dialysis.

15. A system for the treatment of blood, comprising an extracorporeal circulation containing a device according to claim 1.

16. A method for treating proinflammatory conditions in patients suffering from chronic kidney failure, cancer or lupus erythematosus, said method comprising inactivating free nucleic acids of said patients by treating blood of said patients with the system of claim 15.

* * * * *